US010595897B2

(12) United States Patent
Geisz et al.

(10) Patent No.: US 10,595,897 B2
(45) Date of Patent: Mar. 24, 2020

(54) METHOD AND SYSTEM FOR MEASURING PRESSURE IN A BODY CAVITY USING A TROCAR

(71) Applicant: Lexion Medical, LLC, St. Paul, MN (US)

(72) Inventors: Carl M. Geisz, Edina, MN (US); Rochelle M. Amann, Mendota Heights, MN (US)

(73) Assignee: Lexion Medical, LLC, St. Paul, MN (US)

( * ) Notice: Subject to any disclaimer, the term of this patent is extended or adjusted under 35 U.S.C. 154(b) by 115 days.

(21) Appl. No.: 15/251,511

(22) Filed: Aug. 30, 2016

(65) Prior Publication Data
US 2018/0055536 A1 Mar. 1, 2018

(51) Int. Cl.
*A61M 37/00* (2006.01)
*A61B 17/34* (2006.01)
*A61M 13/00* (2006.01)
*A61B 90/00* (2016.01)

(52) U.S. Cl.
CPC .......... *A61B 17/34* (2013.01); *A61B 17/3417* (2013.01); *A61B 17/3474* (2013.01); *A61B 17/3494* (2013.01); *A61M 13/003* (2013.01); *A61B 2090/064* (2016.02); *A61M 2202/0225* (2013.01)

(58) Field of Classification Search
CPC ........ A61M 13/003; A61M 2202/0225; A61M 2205/3344; A61M 13/006; A61B 17/3474
See application file for complete search history.

(56) References Cited

U.S. PATENT DOCUMENTS

| 5,209,721 | A | 5/1993 | Wilk |
| 5,328,458 | A | 7/1994 | Sekino et al. |
| 5,389,077 | A | 2/1995 | Melinyshyn |
| 5,427,114 | A | 6/1995 | Colliver |
| 5,676,155 | A | 10/1997 | Novak et al. |
| 6,295,877 | B1 | 10/2001 | Aboul-Hosn |

(Continued)

FOREIGN PATENT DOCUMENTS

| DE | 43 06 629 A1 | 9/1994 |
| EP | 1 109 486 | 5/2000 |

(Continued)

OTHER PUBLICATIONS

PCT Notification of Transmittal of the International Search Report and the Written Opinion of the International Searching Authority, or the Declaration; Application No. PCT/US2017049070, dated Nov. 2, 2017.

(Continued)

*Primary Examiner* — Rebecca E Eisenberg
(74) *Attorney, Agent, or Firm* — Baker Botts L.L.P.

(57) ABSTRACT

According to one embodiment, a method includes positioning a portion of a trocar into a patient cavity and inserting a surgical instrument into the trocar. The method also includes measuring, by a pressure sensor disposed within the trocar, a pressure within the trocar. The measured pressure is indicative of a pressure in the patient cavity. The method also includes supplying, based at least in part on the measured pressure, an insufflation gas to the patient cavity by providing the insufflation gas through the trocar.

28 Claims, 5 Drawing Sheets

(56) References Cited

U.S. PATENT DOCUMENTS

| | | |
|---|---|---|
| 6,299,592 B1 | 10/2001 | Zander |
| 6,905,489 B2 | 6/2005 | Mantell |
| 7,285,112 B2 | 10/2007 | Stubbs |
| 7,722,558 B2 | 5/2010 | Ott |
| 8,216,189 B2 | 7/2012 | Stubbs |
| 8,235,940 B2 | 8/2012 | Davis |
| 8,715,219 B2 | 5/2014 | Stearns |
| 9,138,549 B2 | 9/2015 | Pagel et al. |
| 2004/0102733 A1 | 5/2004 | Naimark |
| 2004/0204671 A1 | 10/2004 | Stubbs et al. |
| 2005/0115043 A1 | 6/2005 | Maeshima |
| 2007/0088275 A1 | 4/2007 | Stearns et al. |
| 2007/0088276 A1 | 4/2007 | Stubbs et al. |
| 2009/0270794 A1 | 10/2009 | Mantell |
| 2010/0078017 A1 | 4/2010 | Andrieux et al. |
| 2011/0071359 A1 | 3/2011 | Bonadio et al. |
| 2011/0218484 A1* | 9/2011 | Zemlok ............ A61M 13/00 604/26 |
| 2012/0184897 A1 | 7/2012 | Poll |
| 2012/0271234 A1 | 10/2012 | Davis et al. |
| 2012/0316512 A1 | 12/2012 | Ott et al. |
| 2014/0188038 A1* | 7/2014 | Stearns ............ A61M 1/28 604/24 |
| 2015/0290403 A1 | 10/2015 | Torisawa et al. |
| 2016/0220271 A1 | 8/2016 | Mastri |

FOREIGN PATENT DOCUMENTS

| | | |
|---|---|---|
| EP | 2 329 774 A1 | 11/2006 |
| EP | 2 825 840 | 9/2013 |
| WO | WO 2012/128826 A2 | 9/2012 |
| WO | WO 2013/011398 A1 | 1/2013 |

OTHER PUBLICATIONS

Extended European Search Report in European Patent Apptication No. 18175165.2-1113; dated Sep. 28, 2018.

* cited by examiner

METHOD AND SYSTEM FOR MEASURING PRESSURE IN A BODY CAVITY USING A TROCAR

TECHNICAL FIELD

The present disclosure relates generally to medical procedures and more particularly to a method and system for measuring pressure in a body cavity using a trocar.

BACKGROUND

Laparoscopic surgery is a standard procedure in hospitals. Abdominal and chest cavity operations are being performed with instruments inserted through small incisions into interior portions of the body. Such laparoscopic procedures are now considered the treatment of choice for operations such as the removal of the gall bladder, spleen, adrenal glands, uterus, and ovaries. These laparoscopic procedures are accomplished via access through a device typically known as a trocar.

A trocar facilitates the introduction of laparoscopic instruments into the abdomen or chest of the body. These instruments are typically introduced into regions under fluid pressure. Providing a fluid into a body cavity is referred to as insufflation and the fluid, often a gas, is referred to herein as an insufflation gas. The purpose of using such a device is to inflate or distend the body cavity to (1) allow the surgeon to explore the area in which the surgery will be performed and (2) provide a view of the site to be treated or observed. These trocars typically also allow for the insertion of an instrument via the innermost tube of the trocar. Examples of one or more trocars are provided in U.S. Pat. No. 8,715,219 (the '219 Patent), U.S. Pat. No. 7,285,112 (the '112 Patent), and U.S. Pat. No. 8,216,189 (the '189 Patent), which are hereby incorporated by reference as if fully set forth herein.

Currently, insufflation is performed by providing a regulated pressurized insufflation gas to the peritoneal cavity via a cannula of the trocar. This insufflation gas, typically carbon dioxide, is supplied to a connection on the trocar tube by a flexible hose attached thereto by an insufflator. Accurate control of the pressure inside the body cavity is important because it can prevent loss of visualization thru the scope during the surgical procedure. Loss of visualization can slow down the surgery and is also potentially dangerous for the patient as the sharp surgical instruments can no longer be seen by the surgeon.

SUMMARY

According to one embodiment, a method includes positioning a portion of a trocar into a patient cavity and inserting a surgical instrument into the trocar. The method also includes measuring, by a pressure sensor disposed within the trocar, a pressure within the trocar. The measured pressure is indicative of a pressure in the patient cavity. The method also includes supplying, based at least in part on the measured pressure, an insufflation gas to the patient cavity by providing the insufflation gas through the trocar.

According to another embodiment, a trocar assembly includes an inner tubular member formed with an opening adapted to provide access for one or more surgical instruments during a surgical procedure, an outer tubular member disposed about the inner tubular member, and a pressure sensor disposed within the inner tubular member.

The teachings of the disclosure provide one or more technical advantages. Embodiments of the disclosure may have none, some, or all of these advantages. For example, in some embodiments, a method and apparatus for measuring pressure in a patient cavity is provided that allows more accurate assessment of the pressure in a patient cavity due to in part to the proximity of the pressure sensor to the patient cavity. Also, it is out of the gas flow stream which can create inaccurate pressure readings.

Other advantages will be apparent to those of skill in the art.

BRIEF DESCRIPTION OF THE DRAWINGS

For a more complete understanding of embodiments of the disclosure and the potential advantages thereof, reference is now made to the following written description taken in conjunction with the accompanying drawings, in which.

DETAILED DESCRIPTION OF THE DRAWINGS

The teachings of the present disclosure recognize that controlling pressure in a body cavity may be effected more advantageously by measuring a pressure through a pressure sensor disposed within a trocar disposed within the body cavity and providing the measured pressure to a controller that can appropriately supply pressurized insufflation fluid to the body cavity. Measuring pressure using a pressure sensor disposed within the trocar provides a more accurate indication of the pressure in the body cavity and can alleviate pressure control problems that may be experienced through other techniques. Example embodiments are best understood by referring to FIGS. 1A through 5 of the drawings and the description below, like numerals being used for like and corresponding parts of the various drawings.

Figure 1A:
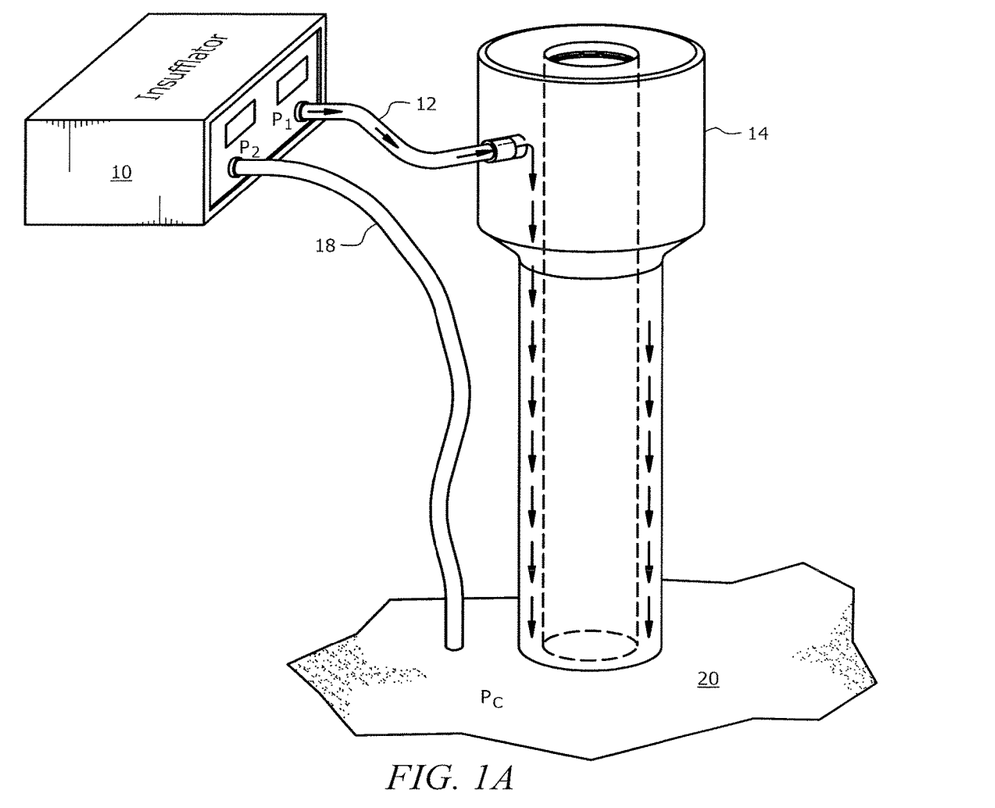
FIG. 1A is a schematic diagram illustrating the control of pressure in a body cavity according to a traditional approach.
Figure 1B:
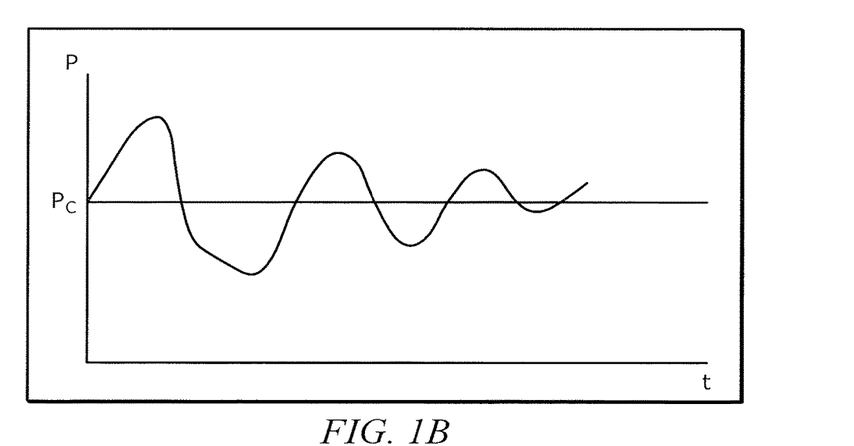
FIG. 1B is a graph illustrating pressure versus time for an example operation of the system of FIG. 1A.

FIG. 1A is a schematic diagram illustrating the control of pressure in a body cavity according to a traditional approach, and FIG. 1B is a graph illustrating pressure versus time for an example operation of the system of FIG. 1A. FIG. 1A shows an insufflator 10 connected to a patient, or body, cavity 20 through conduit 12 and a trocar 14. FIG. 1A also illustrates an alternative conduit 18, through which pressure can be measured.

It is desirable to control the pressure within body cavity 20, referred to as Pc, during an operation. One traditional approach for such pressure control is to provide an insufflation gas to body cavity 20 by insufflator 10, through conduit 12 and trocar 14. In some implementations, insufflator 10 operates on an on/off basis, and the pressure Pc in body cavity 20 is desirably controlled based on the actual pressure Pc in body cavity 20. The traditional control approach, however, is to control supply of insufflation gas from insufflator 10 to body cavity 20 based on a pressure P1, measured at insufflator 10. This pressure P1 is the pressure where conduit 12 meets insufflator 10, and thus serves as a proxy for pressure Pc in patient cavity 20. Due to pressure losses between insufflator 10 and patient cavity 20, the measured pressure P1 is not the same as the actual pressure Pc in patient cavity 20, particularly since pressurized insufflation gas is provided by insufflator 10 through conduit 12. As an alternative traditional method, separate conduit 18 is used to measure P2, which is the pressure where conduit 18 meets insufflator 12. Unlike conduit 12, pressurized insufflation gas is not provided through this conduit 18. Thus, P2 is a better indication of the pressure Pc in patient cavity 20 than P1 is. Nevertheless, both approaches are not as accurate as may be desired and can lead to undesirable results, such as those shown in FIG. 1B. Further, pressure control can become inaccurate or inoperable if conduit 18 becomes clogged or disconnected.

In FIG. 1B, pressure fluctuations over time are shown that can result from both of these traditional control procedures. These fluctuations occur due to differences between the actual Pc in body cavity 20 and P1 and P2. At high leak rates in the patient cavity they can prevent loss of visualization thru the scope during the surgical procedure. Loss of visualization can slow down the surgery, and is also potentially dangerous for the patient as the sharp surgical instruments can no longer be seen by the surgeon.

According to the teachings of the present disclosure, better pressure control of the pressure in a patient or body cavity can be achieved through use of a pressure sensor disposed in a trocar in the patient cavity, such as trocar 16. Disposing a pressure sensor in the trocar allows measurement of pressure at a location much closer to the patient cavity and therefore provides a better basis for determining the actual pressure in the patient cavity, and thus better pressure control.

Figure 2A:
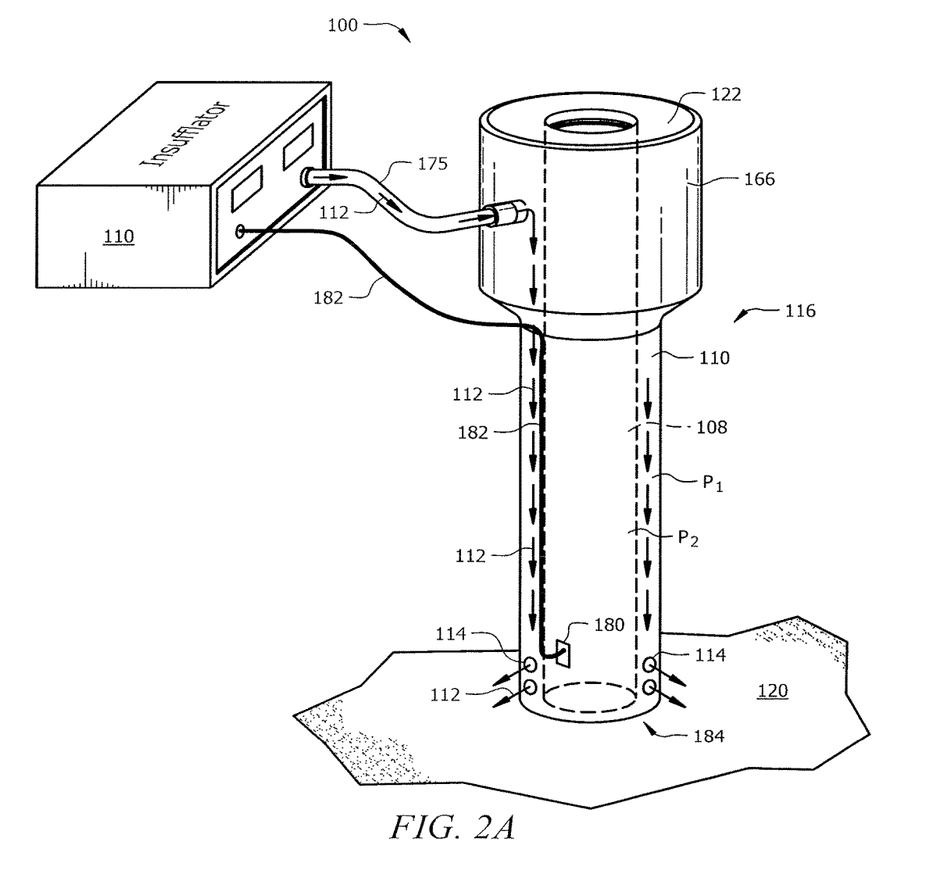
FIGS. 2A and 2B are schematic diagrams of a system for measuring pressure in a body cavity using a trocar.
Figure 2B:
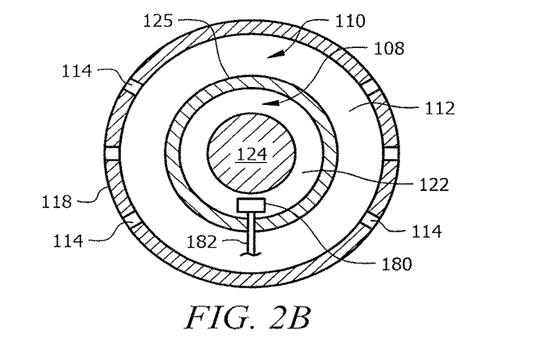

FIGS. 2A and 2B illustrate one embodiment of a system 100 for controlling pressure Pc in a patient or body cavity 120. System 100 includes a trocar 116, an insufflator 110, a conduit 175 for supplying insufflation gas to a portion of trocar 116, a pressure sensor 180 disposed within trocar 116, and a conductive connection 182, providing an electrical connection between pressure sensor 180 and insufflator 110. A distal end 184 of trocar 116 is inserted into patient cavity 120 while the proximal end 122 allows an instrument 124 to be inserted such that trocar 116 provides access to body cavity 120 for the instrument 124. Suitable seals may be positioned in or around trocar 116 for preventing or reducing leakage of fluid out of trocar 116. Patient cavity 120 may be accessed through an incision made with an obturator, which may be included in the same kit or package with trocars described herein.

Trocar 116 is formed with an inner tubular member, or inner lumen, 108 and an outer tubular member, or outer lumen, 110 in this embodiment. However, trocars without separate inner and outer lumens may also be used. Inner lumen 108 is separated from outer lumen 110 by an inner wall 125. Outer lumen 110 is surrounded by an outer wall 118. Outer wall 118 may be formed with one or more holes or apertures 114 near a distal end 162 of trocar 116. Insufflator 110 is a source of insufflation gas and may include appropriate control functionality for adjusting the supply of insufflation gas, such as in response to receiving signals indicative of the pressure in the body cavity. A surgical instrument 124 may be positioned within inner lumen 108 to allow access to patient cavity 120 by a surgeon using surgical instrument 124. Electrical connection 182, which may be an electrical wire or any other suitable form of electrical connection, can be disposed in any suitable location within trocar 116, including in inner lumen 108 or outer lumen 110. Placement of electrical connection 182 primarily within outer lumen 110 provides an additional advantage of protecting electrical connection 182 from possible damage by instrument 124.

According to the operation of one embodiment, insufflation gas 102, which in one embodiment is carbon dioxide, is delivered by insufflator 110 to patient cavity 120 through conduit 175 and outer lumen 110, as indicated by arrows 112. Insufflation gas 102 enters patient cavity 120 via apertures 114 in outer wall 118 of the trocar 116. Pressure is measured by pressure sensor 180 within inner lumen 108 of trocar 124, providing an approximation of the pressure Pc within body cavity 120. The measured pressure is communicated to insufflator 110 through electrical connection 182 through outer lumen 110, in this example. In one embodiment, pressure sensor 180 electrically couples to electrical connection 182 through apertures, although other forms of electrical coupling may be used, including wireless coupling. Based on the measured pressure, insufflator 110 may adjust the pressure Pc in body cavity 180 by, for example, providing or not providing additional insufflation gas 102 to body cavity 120 or by adjusting the pressure or valve flow at which insufflation gas 102 is provided by insufflator 110. Any desired form of control may be used by insufflator, including on/off control, P, P-D, and P-I-D control approaches. By measuring the pressure near the body cavity Pc through a pressure sensor disposed within trocar 116, better control of the pressure within body cavity 120 can be achieved, and undesirable cycling such as that shown in FIG. 1B can be reduced.

Figure 3:
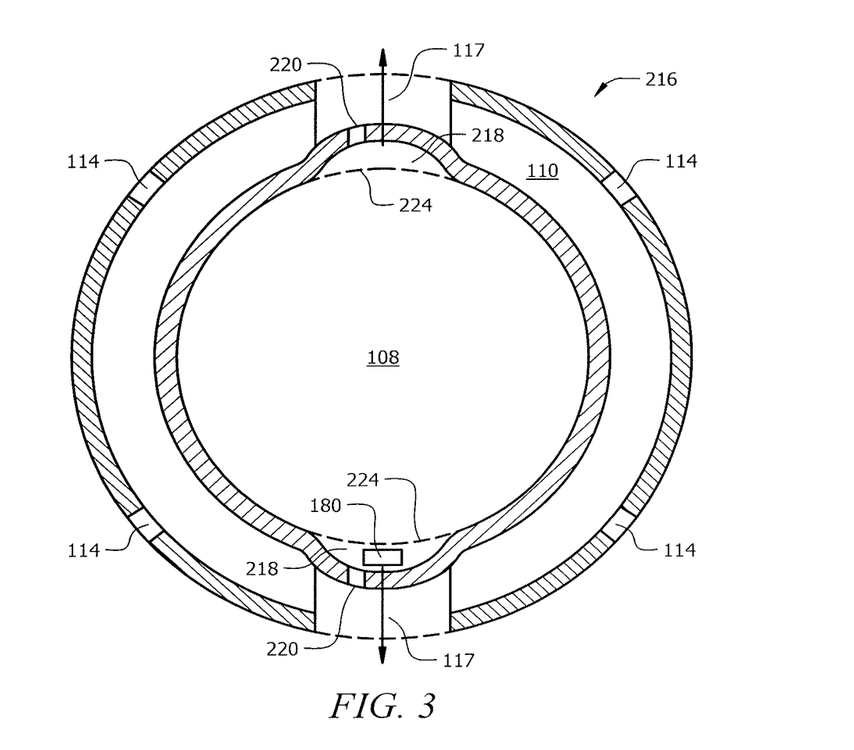
FIG. 3 is a cross sectional diagram of an alternative embodiment of the system of FIGS. 2A and 2B, showing an example cross section of a trocar.
Figure 4A:
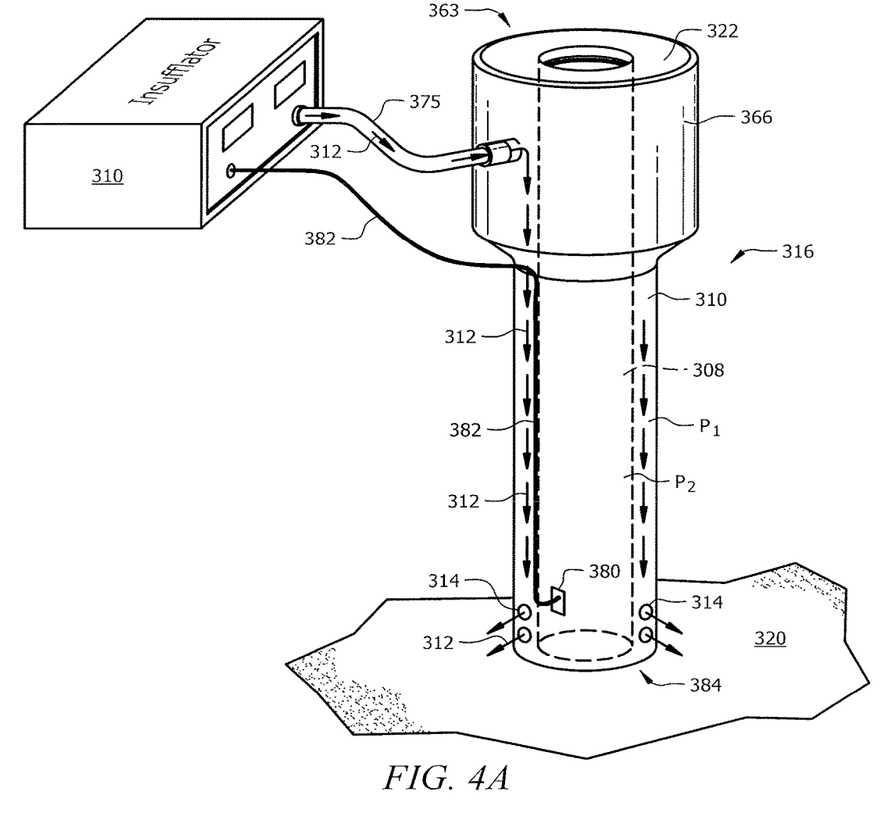
FIGS. 4A and 4B illustrate an alternative embodiment of a system for measuring pressure in a body cavity using a trocar with an outer tubular member having first and second channels.
Figure 4B:
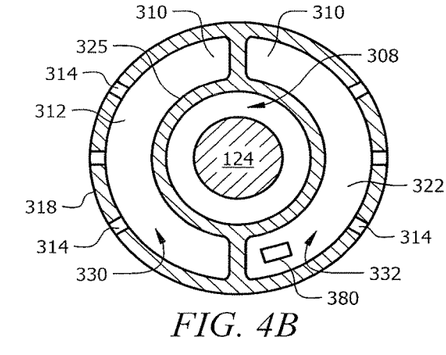
Figure 5:
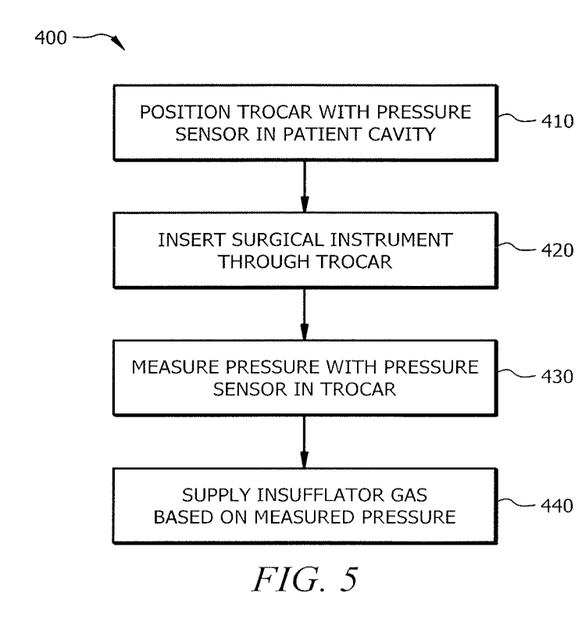
FIG. 5 is a flow chart illustrating a method for measuring pressure in a body cavity using a trocar.

Additional details and embodiments of systems and methods for providing pressure control of the pressure in a patient cavity are described below. FIG. 3 illustrates example details of portions of the system of FIGS. 2A and 2B, according to one embodiment. FIGS. 4A and 4B illustrate an alternative embodiment of a system for measuring pressure in a body cavity using a trocar with an outer tubular member having first and second channels, while FIG. 5 illustrates a method for controlling pressure in a body cavity.

FIG. 3 is a cross sectional diagram near the distal end 184 of one embodiment of a trocar 216 that may be used in the system of FIGS. 2A and 2B. Similar parts to those of trocar 116 have like reference numerals. As illustrated, trocar 216 includes at least one cutout region 218 into which pressure sensor 180 may be disposed. Placement of pressure sensor 180 in cutout region 218 protects pressure sensor 180 from damage that may occur when an instrument, such as instrument 124, is placed within inner lumen 108 of trocar. In this example embodiment cutout region 218 also protrudes into an area where the outer lumen 110 would otherwise be formed. The dotted line 224 forming part of cutout region 218 represents the missing portion of a generally circular inner lumen that would be formed without cutout region 218. Thus, this is one example of a configuration of cutout region 218 in which disposing pressure sensor 180 within cutout region 218 would make pressure sensor 180 generally inaccessible to an instrument 124 with a generally cross sectional area to protect pressure sensor 180 from damage. The cutout regions 218 also ensure that the obturator and/or instruments do not close off the inner lumen 108 from being in intimate contact with the body cavity 120.

In this embodiment, passages 220 between inner lumen 108 and outer lumen 110 are provided to allow gas flow in the event that inner lumen 108 becomes blocked, as indicated by arrows 117. The passages 220 and cutoffs 218 prevent closing off the pressure sensor from the body cavity 120.

FIGS. 4A and 4B illustrate another embodiment of a system 300 for controlling pressure Pc in a patient cavity 320 that uses a trocar having an inner lumen and an outer lumen with a plurality of chambers. System 300 is analogous to system 100, including a trocar 316, an insufflator 310, a conduit 312 for supplying insufflation gas to a portion of trocar 316, a pressure sensor 380 disposed within trocar 316, and a conductive connection 382, providing an electrical connection between pressure sensor 380 and insufflator 310, with analogous portions of system 100 and system 300 having like reference numerals but trocar 316 is analogous to trocar 116, with analogous portions having analogous reference numerals, except that trocar 316 is formed with an inner lumen 308 and an outer lumen 310 having a plurality of chambers 330, 332. Outer wall 318 is formed with one or more holes or apertures 314 near a distal end 362 of trocar 306 that are associated with chamber 330. Outer wall 118 may also be formed with one or more holes or apertures 315 proximate distal end 362 of trocar 306 that are associated with chamber 332. Conductive connection 382 may be disposed primarily in chamber 330, 332 of out lumen 310, in inner lumen 308, or in other suitable locations.

Providing separate chambers 330 and 332 in outer lumen 310 allows placement of pressure sensor 380 in one of the outer chambers 330, 332 and allows supplying insufflation gas in the other outer chamber 330, 332. This protects pressure sensor 380 from damage that could potentially be caused by instrument 124 due to insertion into inner lumen 108, while at the same time isolates pressure sensor 380 from supplied insufflation gas 312, which might otherwise adversely affect the accuracy of the pressure measured by pressure sensor 380. In general, measuring pressure by pressure sensor 380 in a location within trocar 380 that does not also provide a conduit for insufflation gas allows a more accurate estimation of Pc in patient cavity 320 because flow of gas creates a pressure drop along its path. This pressure drop required for gas to flow would create inaccurate pressure readings at the pressure sensor 380.

FIG. 5 is a flowchart illustrating a method of controlling pressure in a patient cavity. At step 410, a trocar is disposed into a patient cavity. In some embodiments, the trocar may be formed with an inner tubular member and an outer tubular member. In some of these embodiments, the outer tubular member may be formed with multiple separate chambers and in some embodiments the outer tubular member has only one distinct chamber. A pressure sensor is located within the trocar. In some embodiments the pressure sensor may be located in the inner tubular member or the outer tubular member. In some embodiments the pressure sensor is located near a distal end of the trocar, near the patient cavity, and also located in a location inaccessible to a surgical instrument that is inserted into the inner tubular member. At step 420, the surgical instrument is inserted into the trocar. At step 430, a pressure is measured by the pressure sensor disposed within the trocar, which is indicating of a pressure in the patient cavity. At step 440, based at least in part on the measured pressure, an insufflation gas is supplied to the patient cavity by providing the insufflation gas through the trocar. In one example, the pressure in the patient cavity can be increased by supplying more insufflation gas or by supplying insufflation gas at a higher pressure. Conversely, the pressure in patient cavity can be reduced by halting or reducing the flow of insufflation gas or by reducing the pressure at which the insufflation gas is supplied. The above steps may be performed in any desired order and may not necessarily be performed sequentially. For example, the pressure may be measured before, after, and/or during insertion of the surgical instrument. As another example, insufflation gas may be supplied before, during, and/or after pressure measurement.

Thus, the systems of FIG. 2A through 5 provide more accurate control of pressure in a patient cavity through use of a pressure sensor disposed within a trocar.

Additional details of systems 100 and 300 are described below for insufflation gas 102, insufflation gas source 170, trocars 116 and 316, open gas tubing connection 120, connection 164, conduit 175, conduit 185, and surgical instrument 124.

Insufflation gas 102 may be any suitable gas used for insufflation purposes. In one example, insufflation case is carbon dioxide. Insufflation gas source 170 may be any suitable source of insufflation gas 102 at any suitable pressure.

Trocars 116, 216, and 316 may be any suitable as described herein. All trocars described herein may be open or closed at the distal end, as the application of the trocar would allow. Further, the trocars may or may not include apertures in their inner wall separating the outer lumen from the inner lumen. Further, all trocars described herein may be formed according to features described in the '219 Patent, the '112 Patent, and/or the '186 Patent. Further, trocars 116 and 316 may be formed with a heater and/or humidifier therein.

Conduit 175 may be any suitable conduit for providing an insufflation gas to a portion of a trocar. An example of conduit 175 includes flexible PVC tubing.

Conduit 185 may be any suitable conduit for providing a vacuum to a portion of a trocar. An example of conduit 185 is flexible PVC tubing.

Surgical instrument 124 may be any suitable instrument that may be used in surgery, including an obturator used to make an incision to obtain access to a body cavity.

Modifications, additions, or omissions may be made to systems 100, 300 without departing from the scope of the invention. The components of these systems may be integrated or separated. Moreover, the operations of these systems may be performed by more, fewer, or other components.

Although FIGS. 2A through 5 have been described above as including particular steps and/or components, the method and systems of these FIGURES may include any combination of any of the described steps and/or components and any of the options or features described herein, as would be understood by one of ordinary skill in the art. For example, any of the steps, options, or features described herein may be utilized in combination with the illustrated embodiments of FIGS. 2A through 5 and/or any number of the other steps, options, or features also described herein, as would be understood by one of ordinary skill in the art.

Although the embodiments in the disclosure have been described in detail, numerous changes, substitutions, variations, alterations, and modifications may be ascertained by those skilled in the art. It is intended that the present disclosure encompass all such changes, substitutions, variations, alterations, and modifications.

What is claimed is:

1. A method comprising:
   positioning a portion of a trocar into a patient cavity, the trocar comprising an inner tubular member and an outer tubular member disposed about the inner tubular member;

inserting a surgical instrument into the inner tubular member of the trocar;

measuring, by a pressure sensor disposed within the inner tubular member of the trocar and being in direct pressure contact with the patient cavity, a pressure within the inner tubular member of the trocar, the measured pressure being indicative of a pressure in the patient cavity; and supplying, based at least in part on the measured pressure, an insufflation gas to the patient cavity by providing the insufflation gas through the outer tubular member of the trocar.

2. The method of claim 1, wherein the pressure sensor is disposed in a portion of the trocar that is not accessible by the surgical instrument.

3. The method of claim 2, wherein a cross section of the inner tubular member is formed with a cutout region and the pressure sensor is disposed within the cutout region.

4. The method of claim 1, wherein the pressure sensor is electrically connected to an insufflator for supplying the insufflation gas to the patient cavity, the electrical connection comprising a wire disposed at least partially within the inner tubular member of the trocar.

5. The method of claim 1, and further comprising controlling the pressure in the patient cavity based on the pressure measured by the pressure sensor disposed in the trocar.

6. The method of claim 5, wherein controlling the pressure in the patient cavity comprises maintaining a substantially constant pressure in the patient cavity.

7. The method of claim 1, wherein the pressure sensor is electrically connected to an insufflator for supplying the insufflation gas to the patient cavity, the electrical connection comprising a wire disposed at least partially within the outer tubular member of the trocar.

8. The method of claim 1, wherein the outer tubular member is formed with apertures in a side wall of the outer tubular member for allowing the insufflation case to flow into the patient cavity.

9. The method of claim 1, wherein the inner tubular member is formed with apertures in a side wall of the inner tubular member for allowing insufflation gas to flow between the inner and outer tubular members.

10. A method comprising:
positioning a portion of a trocar into a patient cavity;
inserting a surgical instrument into the trocar;
measuring, by a pressure sensor disposed within the trocar and being in direct pressure contact with the patient cavity, a pressure within the trocar, the measured pressure being indicative of a pressure in the patient cavity; and
supplying, based at least in part on the measured pressure, an insufflation gas to the patient cavity by providing the insufflation gas through the trocar.

11. The method of claim 10, wherein
the trocar comprises an inner tubular member and an outer tubular member disposed about the inner tubular member;
inserting the surgical instrument into the trocar comprises inserting the surgical instrument into the inner tubular member;
the pressure sensor is disposed in the inner tubular member of the trocar and measuring a pressure within the trocar comprises measuring a pressure within the inner tubular member; and
supplying the insufflation gas comprises supplying the insufflation gas through the outer tubular member.

12. The method of claim 11, wherein the outer tubular member is formed with apertures in a side wall of the outer tubular member for allowing the insufflation case to flow into the patient cavity.

13. The method of claim 11, wherein the inner tubular member is formed with apertures in a side wall of the inner tubular member for allowing insufflation gas to flow between the inner and outer tubular members.

14. The method of claim 10, wherein the pressure sensor is disposed in a portion of the trocar that is not accessible by the surgical instrument.

15. The method of claim 10, wherein
the trocar comprises an inner tubular member and an outer tubular member disposed about the inner tubular member; and
the pressure sensor is disposed in a portion of the inner tubular member that is not accessible by the surgical instrument.

16. The method of claim 15, wherein a cross section of the inner tubular member is formed with a cutout region and the pressure sensor is disposed within the cutout region.

17. The method of claim 10, wherein
the trocar comprises an inner tubular member and an outer tubular member disposed about the inner tubular member, the outer tubular member having at least a first chamber and a second chamber separated from the first chamber; and
the pressure sensor is disposed in the first chamber and the insufflation gas is supplied through the second chamber.

18. The method of claim 10, wherein the pressure sensor is electrically connected to an insufflator for supplying the insufflation gas to the patient cavity, the electrical connection comprising a wire disposed at least partially within the trocar.

19. The method of claim 10, and further comprising controlling the pressure in the patient cavity based on the pressure measured by the pressure sensor disposed in the trocar.

20. The method of claim 19, wherein controlling the pressure in the patient cavity comprises maintaining a substantially constant pressure in the patient cavity.

21. A trocar assembly comprising:
an inner tubular member formed with an opening adapted to provide access for one or more surgical instruments during a surgical procedure;
an outer tubular member disposed about the inner tubular member; and
a pressure sensor disposed within the inner tubular member and configured to be in direct pressure contact with a patient cavity.

22. The trocar assembly of claim 21, wherein the inner tubular member is formed with a cutout and the pressure sensor is disposed within the cutout of the inner tubular member.

23. The trocar assembly of claim 21, and further comprising an electrical wire connected to the pressure sensor and extending to an insufflator.

24. The trocar assembly of claim 21, wherein the electrical wire is disposed partially in the outer tubular member.

25. The trocar assembly of claim 21, wherein the outer tubular member has at least a first chamber and a second chamber separated from the first chamber.

26. The trocar assembly of claim 21, and further comprising the insufflator.

27. The trocar assembly of claim 21, wherein the outer tubular member is formed with apertures in a side wall of the outer tubular member for allowing the insufflation case to flow into the patient cavity.

28. The trocar assembly of claim 21, wherein the inner tubular member is formed with apertures in a side wall of the inner tubular member for allowing insufflation gas to flow between the inner and outer tubular members.

* * * * *